(12) United States Patent
Engelbart et al.

(10) Patent No.: US 7,372,556 B2
(45) Date of Patent: May 13, 2008

(54) APPARATUS AND METHODS FOR INSPECTING A COMPOSITE STRUCTURE FOR INCONSISTENCIES

(75) Inventors: Roger W Engelbart, St. Louis, MO (US); Reed Hannebaum, Belleville, IL (US); Tim Pollock, Ballwin, MO (US); Sam Orr, Barnhart, MO (US); Jeff Putnam, St. Louis, MO (US); Eric Rector, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 270 days.

(21) Appl. No.: 11/264,076

(22) Filed: Oct. 31, 2005

(65) Prior Publication Data

US 2007/0097359 A1 May 3, 2007

(51) Int. Cl.
*G01N 11/00* (2006.01)
(52) U.S. Cl. .................. 356/237.1; 356/237.5
(58) Field of Classification Search .. 356/237.1–237.5, 356/608; 438/131; 430/30; 382/145, 148, 382/141
See application file for complete search history.

(56) References Cited

U.S. PATENT DOCUMENTS

| | | | |
|---|---|---|---|
| 3,879,245 A | | 4/1975 | Fetherson et al. |
| 4,037,941 A | * | 7/1977 | Belleson et al. ............ 359/218 |
| 4,064,534 A | | 12/1977 | Chen et al. |
| 4,310,132 A | | 1/1982 | Robinson et al. |
| 4,548,859 A | | 10/1985 | Kline et al. |
| 4,601,577 A | * | 7/1986 | Gotou et al. .............. 356/237.5 |
| 4,608,220 A | | 8/1986 | Caldwell et al. |
| 4,693,678 A | | 9/1987 | Von Volkli |
| 4,699,683 A | | 10/1987 | McCowin |
| 4,760,444 A | | 7/1988 | Nielson et al. |
| 4,780,262 A | | 10/1988 | Von Volkli |
| 4,790,898 A | | 12/1988 | Woods |
| 4,830,298 A | | 5/1989 | Van Blunk |
| 4,877,471 A | | 10/1989 | McCowin et al. |
| 4,941,182 A | | 7/1990 | Patel |
| 5,024,399 A | | 6/1991 | Barquet et al. |

(Continued)

FOREIGN PATENT DOCUMENTS

EP          0 319 797 A2     6/1989

(Continued)

OTHER PUBLICATIONS

Office Action Summary from the USPTO mailed Oct. 18, 2006 in reference to U.S. Appl. No. 10/846,974, filed May 14, 2004, first named inventor Roger W. Engelbart.

(Continued)

*Primary Examiner*—Sang H. Nguyen
(74) *Attorney, Agent, or Firm*—Harness, Dickey & Pierce, P.L.C.

(57) ABSTRACT

A system and method of inspecting material laid by a material placement machine. Light is directed onto the material in a direction essentially normal to the material to illuminate a section of the material. Laser energy is projected onto the section at an angle predetermined to reveal inconsistencies in the section. This system provides improved illumination for material widths exceeding six inches and is scalable for inspecting various material widths.

19 Claims, 3 Drawing Sheets

U.S. PATENT DOCUMENTS

| | | | |
|---|---|---|---|
| 5,058,497 | A | 10/1991 | Bishop et al. |
| 5,198,983 | A | 3/1993 | Blake et al. |
| 5,278,012 | A * | 1/1994 | Yamanaka et al. ............ 430/30 |
| 5,337,647 | A | 8/1994 | Roberts et al. |
| 5,439,549 | A | 8/1995 | Fryc et al. |
| 5,450,147 | A | 9/1995 | Dorsey-Palmateer |
| 5,518,208 | A | 5/1996 | Roseburg |
| 5,540,126 | A | 7/1996 | Piramoon |
| 5,562,788 | A | 10/1996 | Kitson et al. |
| 5,651,600 | A | 7/1997 | Dorsey-Palmateer |
| 5,683,646 | A | 11/1997 | Reiling, Jr. |
| 5,684,530 | A * | 11/1997 | White ........................ 348/131 |
| 5,700,337 | A | 12/1997 | Jacobs et al. |
| 5,746,553 | A | 5/1998 | Engwall |
| 5,804,276 | A | 9/1998 | Jacobs et al. |
| 5,814,386 | A | 9/1998 | Vasiliev et al. |
| 5,825,495 | A | 10/1998 | Huber |
| 5,871,117 | A | 2/1999 | Protasov et al. |
| 5,917,588 | A | 6/1999 | Addiego |
| 5,963,660 | A | 10/1999 | Koontz et al. |
| 5,979,531 | A | 11/1999 | Barr et al. |
| 6,012,883 | A | 1/2000 | Engwall et al. |
| 6,013,341 | A | 1/2000 | Medvedev et al. |
| 6,028,673 | A * | 2/2000 | Nagasaki et al. ............ 356/608 |
| 6,045,651 | A | 4/2000 | Kline et al. |
| 6,074,716 | A | 6/2000 | Tsotsis |
| 6,086,696 | A | 7/2000 | Gallagher |
| 6,112,792 | A | 9/2000 | Barr et al. |
| 6,168,358 | B1 | 1/2001 | Engwall et al. |
| 6,205,239 | B1 | 3/2001 | Lin et al. |
| 6,364,250 | B1 | 4/2002 | Brinck et al. |
| 6,369,492 | B1 | 4/2002 | Sugimoto |
| 6,390,169 | B1 | 5/2002 | Johnson |
| 6,451,152 | B1 | 9/2002 | Holmes et al. |
| 6,480,271 | B1 | 11/2002 | Cloud et al. |
| 6,547,769 | B2 | 4/2003 | Van Tassel et al. |
| 6,552,783 | B1 * | 4/2003 | Schmidt et al. .......... 356/237.4 |
| 6,633,375 | B1 * | 10/2003 | Veith et al. ............... 356/237.4 |
| 6,639,662 | B2 | 10/2003 | Vaez-Iravani et al. |
| 6,648,273 | B2 | 11/2003 | Anast |
| 6,692,681 | B1 | 2/2004 | Lunde |
| 6,721,047 | B2 * | 4/2004 | Shimoda et al. .......... 356/237.5 |
| 6,725,123 | B1 | 4/2004 | Denuell |
| 6,799,619 | B2 | 10/2004 | Holmes et al. |
| 6,814,822 | B2 | 11/2004 | Holmes |
| 6,871,684 | B2 * | 3/2005 | Engelbart et al. ............ 156/361 |
| 2002/0141632 | A1 | 10/2002 | Engelbart et al. |
| 2004/0098852 | A1 | 5/2004 | Nelson |
| 2005/0023414 | A1 | 2/2005 | Braun |
| 2005/0025350 | A1 | 2/2005 | Engelbart et al. |
| 2005/0039842 | A1 | 2/2005 | Clark |
| 2005/0039843 | A1 | 2/2005 | Johnson et al. |
| 2005/0039844 | A1 | 2/2005 | Engwall et al. |
| 2005/0102814 | A1 | 5/2005 | Anderson et al. |
| 2005/0117793 | A1 | 6/2005 | Engelbart et al. |
| 2005/0203657 | A1 | 9/2005 | Engelbart et al. |
| 2005/0225753 | A1 | 10/2005 | Engelbart et al. |
| 2005/0263645 | A1 | 12/2005 | Johnson et al. |

FOREIGN PATENT DOCUMENTS

| | | |
|---|---|---|
| EP | 0 903 574 | 3/1994 |
| EP | 0 833 146 A2 | 1/1998 |
| EP | 1 030 172 | 8/2000 |
| JP | 2001012930 | 1/2001 |
| WO | WO 94/18643 | 8/1994 |
| WO | WO 2004/025385 | 3/2004 |

OTHER PUBLICATIONS

U.S. Appl. No. 10/628,691 entitled Systems and Methods for Identifying Foreign Objects and Debris (FOD) and Defects During Fabrication of a Composite Structure, Engelbart et al., filed Jul. 28, 2003.

Pending U.S. Appl. No. 10/819,084, Turnmire et al., filed Apr. 6, 2004.

Pending U.S. Appl. No. (not yet assigned) entitled Composite Barrel Sections for Aircraft Fuselages and Other Structures, and Methods and Systems for Manufacturing Such Barrel Sections, Biornstad et al., filed May 20, 2004.

Expired U.S. Appl. No. 60/559,890, Biornstad et al., Apr. 6, 2004.

Expired U.S. Appl. No. 60/559,911, Johnson et al., Apr. 4, 2004.

Pending utility U.S. Appl. No. 10/949,848, Stulc, Sep. 23, 2004.

Krupka, R; Walz, T; Ettemeyer, A: "Industrial Applications of Shearography for Inspection of Aircraft Components" Proceedings of the 8th European Conference of Nondestructive Testing< Barcelona (Spain), Jun. 17-21, 2002, 'Online! Jun. 30, 2002, XP002351899 NDT.NET—Feb. 2003, vol. 8, No. 2 Retrieved from the Internet: URL:http://www.ndt.net/articl/ecndt02/484/484.htm> 'retrieved on Oct. 31, 2005!.

BAe 146, Flight International, May 2, 1981, 2 pages.

A Barrelful of Experience, Intervia, May 1992, 2 pages.

Raytheon, Mar. 2000, vol. 4, No. 2, http://www.cts.com/king/vasci/newsletter/vol42.html, 2 pages.

Business Aviation, Jun. 7, 2002, http://www.aviationnow.com/avnow/news/channel_busav.jsp?view=story&id=news/btoyo0607.xml, 1 page.

Sharp et al., "Material Selection/Fabrication Issues for Thermoplastic Fiber Placement", Journal of Thermoplastic Composite Materials, vol. 8; Jan. 1995, p. 2-14.

Advanced Technology Tape Laying for Affordable Manufacturing of Large Composite Structures; http://www.cinmach.com/tech/pdf/TapeLayingGrimshaw.pdf; Michael N. Grimshaw, et al; 11 pages; 2001.

Fiber Placement; http://www.cinmach.com/tech/pdf/asm_chapter_fp.pdf; Don O. Evans; Cincinnati Machine; 3 pages; Handbook of Composites published in 1998.

Automated Tape Laying; http://www.cinmach.com/tech/pdf/Grimshaw%20ASM%20Handbook.pdf; Michael N. Grimshaw; Cincinnati Machine; 6 pages; May 11, 2003.

Raytheon Aircraft's Hawker Horizon Reaches Fuselage Milestone, Raytheon News Release; http://www.beechcraft.de/Presse/2000/100900b.htm; 2 pages; Oct. 9, 2000.

Beechcraft's Composite Challenge, http://www.aerotalk.com/Beech.cfm, 2 pages; Apr. 13, 2003.

http://www.cinmach.com/WolfTracks4-1/MTG-WT7.htm; Premier I Features Lighter, Stronger, All-Composite Fuselage, 1 page; 1998.

htpp://www.cinmach.com/compnews/PressReleases/pr00-11.htm; Raytheon Aircraft Orders Four More Fiber Cincinnati Fiber Placement Systems for Industry's First Composite-Fuselage Business Jets, 1 page; Jul. 20, 2000.

htpp://www.rockymountaincomposites.com/wind-sys.htm: Filament Winding, 1 page; 2000.

\* cited by examiner

APPARATUS AND METHODS FOR INSPECTING A COMPOSITE STRUCTURE FOR INCONSISTENCIES

FIELD

The present disclosure relates generally to automated material placement machines and their use. More particularly (but not exclusively) the present disclosure relates to systems and methods for inspecting material laid by an automated material placement machine.

BACKGROUND

Automated material placement processes and machines are widely used in aerospace and other industries in the fabrication of large composite structures. Systems are available by which automated visual inspection can be performed while the material is being laid. These systems have been shown to be effective in reducing machine down-time for inspection purposes. Current inspection systems, however, have limited effectiveness when used to inspect materials wider than about six inches.

SUMMARY

The present disclosure, in one aspect, is directed to a method of inspecting material laid by a material placement machine. Light is directed onto the material in a direction essentially normal to the material to illuminate a section of the material. Laser energy is projected onto the section at an angle predetermined to reveal inconsistencies in the section.

In another aspect, the disclosure is directed to a system for inspecting material laid by a material placement machine. The system includes a mirror and one or more light sources configured to project light onto the mirror. The mirror is configured to reflect the projected light onto a section of the material in a direction essentially normal to the section. One or more laser sources are configured to project laser energy onto the section at an angle predetermined to reveal inconsistencies in the section.

In yet another aspect, the disclosure is directed to a system for inspecting material laid by a material placement machine. The system includes a mirror suspended over a section of the material that has been laid. The mirror has one or more transparent portions. One or more light sources are configured to project light onto one or more reflective portions of the mirror. The mirror is further configured to reflect the projected light onto the material section in a direction essentially normal to the section. One or more laser sources are configured to project laser energy onto the section at an angle predetermined to reveal inconsistencies in the section. One or more cameras are configured to record the section through the one or more transparent portions of the mirror.

Further areas of applicability of the present disclosure will become apparent from the detailed description provided hereinafter. It should be understood that the detailed description and specific examples, while indicating various preferred embodiments of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

The following description of various embodiments is merely exemplary in nature and is in no way intended to limit the disclosure, its application, or uses.

In some implementations, the disclosure is directed to systems and methods of inspecting material laid by a material placement machine. The placement machine could be, for example, a multi-head tape lamination machine (MHTLM), a fiber placement (FP) machine, or a contour tape lamination (CTL) machine. It should be noted that implementations of the disclosure may be practiced in connection with a wide variety of material placement machines and processes.

Figure 1:
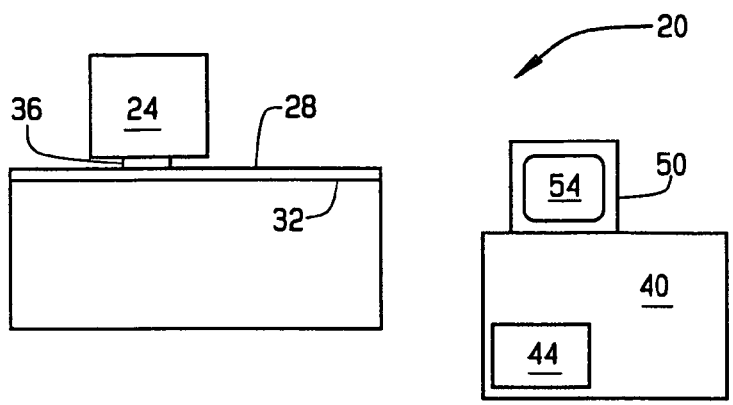
FIG. 1 is a block diagram of a material placement system in accordance with one implementation of the disclosure.

A block diagram of an exemplary material placement system is indicated generally in FIG. 1 by reference number 20. A material placement machine 24 is used to lay down composite material 28 onto a substrate 32 to fabricate a composite structure. The machine 24 includes a roller, compaction shoe and/or other component, numbered as 36 and dependent on the type of placement machine, for laying the material 28 onto the substrate 32. The system 20 includes a processor 40 having a memory and/or storage device 44. The processor 40 is in communication with the machine 24. A user interface 50 may be, e.g., a computer monitor including a display screen 54 and an input device such as a keyboard and mouse (not shown). The user interface 50 is in communication with the processor 40.

Figure 2:
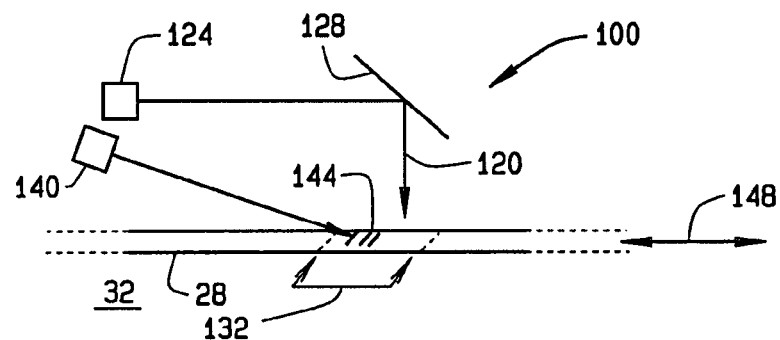
FIG. 2 is a block diagram illustrating a method of inspecting material laid by a material placement system in accordance with one implementation of the disclosure.
Figure 3:
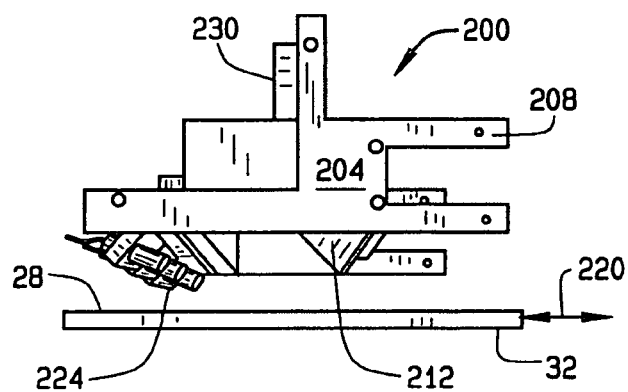
FIG. 3 is a side perspective view of a system for inspecting material laid by a material placement system in accordance with one implementation of the disclosure.
Figure 4:
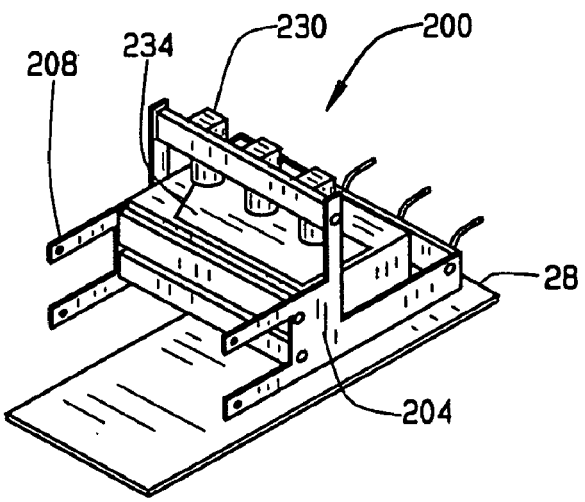
FIG. 4 is a top/side perspective view of a system for inspecting material laid by a material placement system in accordance with one implementation of the disclosure.
Figure 5:
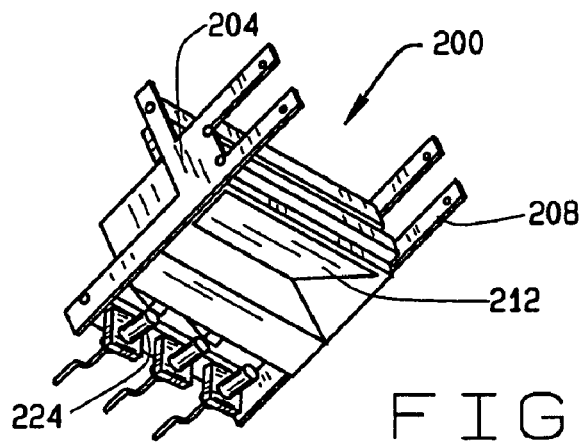
FIG. 5 is a bottom/side perspective view of a system for inspecting material laid by a material placement system in accordance with one implementation of the disclosure.
Figure 6:
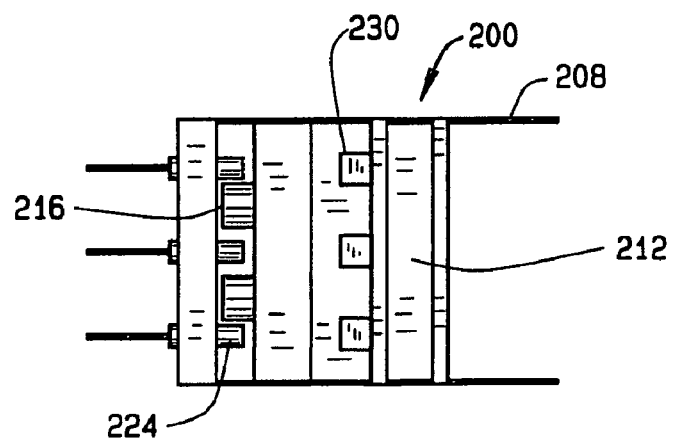
FIG. 6 is a top view of a system for inspecting material laid by a material placement system in accordance with one implementation of the disclosure.
Figure 7:
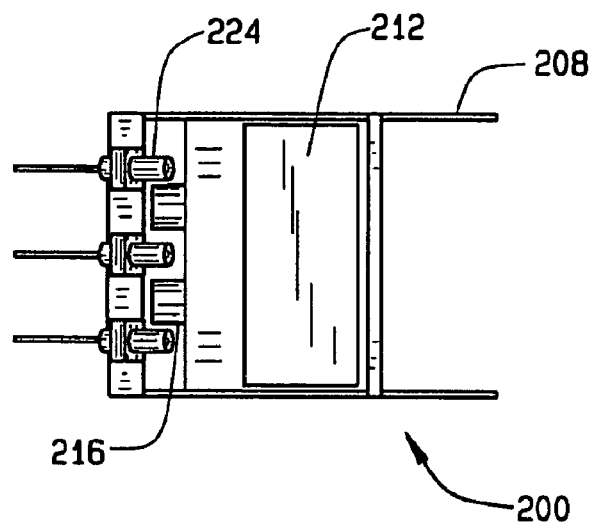
FIG. 7 is a bottom view of a system for inspecting material laid by a material placement system in accordance with one implementation of the disclosure.

One implementation of a method of inspecting material laid by a material placement machine, e.g., the machine 24, is indicated generally in FIG. 2 by reference number 100. A width of the material 28 is newly laid on the substrate 32 by the machine 24. Light is directed onto the material 28 in a direction 120 essentially normal to the material to illuminate the material. Specifically and for example, the light is projected from a light source 124 onto a reflective surface 128 and reflected by the surface 128 onto the material 28 to illuminate a section 132 of the laid material. The method 100 also includes projecting laser energy onto the section 132 at an angle predetermined to reveal inconsistencies in the section 132. In the present implementation, a laser source 140 projects the laser energy as one or more lines 144 onto the section 132. The lines or stripes are projected, for example, across an axis 148 of placement of the material 28. It should be noted that other implementations are contemplated in which different laser patterns and/or laser projection orientations may be used.

The light source 124 above the material 28 may be configured to illuminate a full width of the material 28. The laser striping 144 can reveal gaps and/or overlaps in the material 28. Additionally, the striping can enhance the illumination from the light source 124 and can help reveal such items as fuzz balls, resin balls, and backing materials.

The present method can be implemented in various ways on various placement machines. Additionally, and as further described below, implementations of the present method can be scaled to various widths of material to be inspected. For example, although a single light source 124 and a single laser source 140 are used in the implementation 100, a plurality of light sources and/or a plurality of laser sources may be used in other implementations.

One exemplary embodiment of a system for inspecting material laid by a material placement machine is indicated generally in FIGS. 3-7 by reference number 200. The system 200 includes a frame 204 having brackets 208 configured for attachment to a placement machine, e.g., the machine 24 (shown in FIG. 1). It should be noted that other embodiments of the system 200 could be configured in various ways in relation to material placement machines, dependent on width of material to be inspected and placement machine configuration. For purposes of describing the present embodiment, it shall be assumed that component 36 of the machine 24 is a compaction roller. The frame 204 is configured for attachment, for example, above and behind the compaction roller 36 such that the frame 204 overhangs newly laid material 28. A mirror 212 is mounted in the frame 204, for example, at a 45-degree angle. The mirror 212 is at least partially silvered to provide one or more reflective portions.

A plurality of light sources 216 are mounted, for example, such that they project light essentially parallel to an axis 220 of placement of the material 28. Light from the light sources 216 may be projected toward the mirror 212 and reflected by the mirror reflective portion(s) onto the material 28 in a direction essentially normal to the material.

A plurality of laser sources 224 mounted to the frame 204 are configured to project laser energy directly onto the material 28 at an angle predetermined to reveal inconsistencies in the material. The laser sources 224 may be, for example, Lasaris™ SNF line lasers by StockerYale, Inc. of Salem, N.H.

A plurality of cameras 230 are mounted in the frame 204 above the mirror 212. The cameras 230 are configured to image, through one or more transparent portions 234 of the mirror 212, a section of the material 28 illuminated by the light and laser sources 216 and 224. The cameras 230 may be actuated, for example, by the processor 40, which receives images from the cameras 230 and/or memory 44. The processor 40 may process the images to facilitate reliable detection of inconsistencies.

The cameras 230 are, for example, Sony XC-HR50 cameras, although other cameras could be used. The cameras 230 collectively have fields of view sufficiently broad to image a full width of the newly laid material. A wide range of cameras can be used, including commercially available cameras capable of acquiring black-and-white images. In one embodiment, a camera 230 is a television or other type of video camera having an image sensor and a lens through which light passes when the camera is in operation. Other types of cameras or image sensors can also be used, such as an infrared-sensitive camera, a visible light camera with infrared-pass filtration, a fiber-optic camera, a coaxial camera, charge-coupled device (CCD), or complementary metal oxide semiconductor (CMOS) sensor.

The light and laser sources 218 and 224 are configured to illuminate the full width of the newly laid material 28. The illumination is reflected differently by inconsistencies in the material than by portions of the material that are free of inconsistencies. Such differences in illumination can be captured in images produced by the cameras 230. The frame 204 may be configured to shield the light sources and cameras so as to optimize the quality of imaging by the cameras 230. It should be noted that various lighting and reflective configurations are possible. For example, a half-mirror could be used such that light from light sources is reflected by the mirror onto the material, and the cameras are directed not through, but past the mirror.

In the present configuration, the light sources 216 include high-intensity red LEDs which produce area light. Other or additional types of lighting, including but not limited to fluorescent lights, could be used. The quality and magnitude of surface illumination of the material 28 can be affected by ambient lighting and by reflectivity of the material. Accordingly, in one embodiment, one or more infrared light sources and/or light sources having an infrared component may be used to illuminate dark inconsistencies on a dark background. In other embodiments, a strobe or stroboscopic light source, a noble gas arc lamp (e.g., xenon arc), metal arc lamp (e.g., metal halide) and/or laser (e.g., pulsed laser, solid state laser diode array and/or infrared diode laser array) could be used. Power levels and wavelengths for light source(s) 216 may depend at least in part on the speed and sensitivity of the cameras 230, speed at which the material 28 is being laid, delivery losses, and reflectivity of the material being inspected. For example, in another embodiment, wavelengths and power levels suitable for inspecting highly reflective materials may be employed.

In the configuration shown in FIGS. 3-7, two light sources 216, three laser sources 224, and three cameras 230 are used. Each laser source 224 and camera 230 can cover, e.g., material widths of between about three and four inches. Coverage could be greater or smaller than the foregoing range depending, for example, on lens type, distance between material and cameras and/or laser sources, and other factors. Depending, for example, on a width of material to be inspected and placement system configuration, different numbers of light sources, laser sources and/or cameras could be included to facilitate material inspection. The system 200 thus can be scaled up or down to accommodate different material widths.

When the machine 24 is in operation, motion of the machine may be detected by the processor 40, for example, via a code ring on the compaction roller and photo-interrupter as disclosed in U.S. patent application Ser. No. 10/726,099 entitled "Systems and Methods For Determining Inconsistency Characteristics of a Composite Structure", the disclosure of which is incorporated herein in its entirety. The processor 40 thereby determines that the machine 24 is in operation. The processor 40 actuates the cameras 230 to obtain images at appropriate times based on movement of the machine 24. Specifically and for example, by tracking distances moved by the machine 24, the processor 40 may actuate the cameras 230 to obtain images of material newly placed on the substrate 32 and which is currently being illuminated by the light and laser sources 216 and 224. The processor 40 may receive each image and may assign unique numbers to frames of the image data from the cameras 230. The processor 40 may store image frames in the memory 44 and may use them to track a linear position of the machine 24 as material is placed on the substrate 32.

The processor 40 processes the image data in a frame to detect inconsistencies in the imaged section of material 28. The processor 40 also analyzes and displays selected inconsistencies on the user interface 50. An inconsistency dimension, for example, an inconsistency width, can be determined as follows. After a digital image of an inconsistency has been acquired, a pixel set is selected from the digital image that represents the width of the inconsistency. The pixels in the pixel set are counted, and the count is correlated with distance to determine the inconsistency width.

Figure 8:
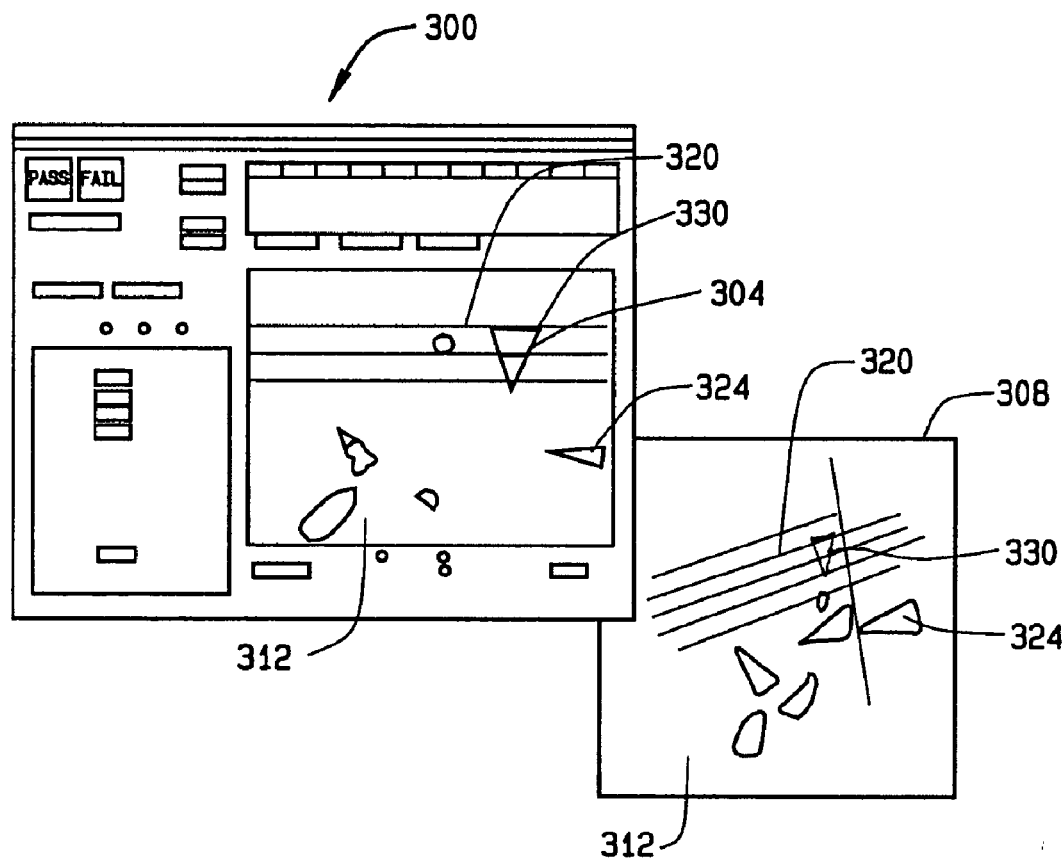
FIG. 8 is an illustration of a section of illuminated material and its image in a frame displayed on a user interface screen in accordance with one implementation of the disclosure.

The processor 40 may receive images from the cameras 230 and/or memory 44 and may process the images to facilitate the reliable detection of inconsistencies. The processor 40 may display information on the user interface display screen 54, for example, as shown in FIG. 8. A window 300 includes a frame 304 showing at least part of a section 308 of material 28 imaged by the cameras 230. For example, an illuminated area 312 of the section 308 is shown in the window 300. Laser lines 320 produced by the laser sources 224 also are visible above the area 312. Inconsistencies 324 may be labeled and are shown in the window 300. A foreign object/debris (FOD) 330 struck by the laser lines 320 may be accentuated by the processor 40 for display in the frame 300. The laser striping 320 can provide a "second-look" enhancement of areas lighted by the light sources 216 and thus can assist in revealing inconsistencies such as fuzz balls, resin balls, and backing materials. It should be noted, however, that although the laser striping 320 strikes the material 28 above the illuminated area 312 in the frame 300, other arrangements of light source and laser source illumination are possible. In some embodiments, illumination from the light and laser sources 216 and 224 could be configured to overlap to a greater degree, or alternatively to strike material farther apart, than as shown in FIG. 8

It should be understood that in various implementations, images from the cameras 230 could be displayed in various ways on the user interface 50. For example, images from two or more cameras 230 could be displayed simultaneously, e.g., side by side in a frame on the screen 54, or sequentially in different frames.

The frame 300 may include a processed or unprocessed camera image. Additionally or alternatively, the frame may include an image that has been binarized. During binarization, all shades of gray above a predetermined threshold value can be changed to white, while all gray shades below the threshold are changed to black to heighten the contrast of inconsistencies and improve the accuracy of inconsistency detection. In other embodiments, the binarization operation need not be performed but instead the raw image, rates of change of the light levels in the raw image, and/or color changes in the images can be used to identify the inconsistencies.

The foregoing systems and methods provide improved illumination and inspection across varying material widths. Various implementations of the disclosure provide the ability to inspect wider bands of material more effectively than possible with current inspection systems, which use low-incident-angle side lighting to illuminate material under inspection. The dual on-axis lighting provided by implementations of the disclosure can provide even illumination across material widths and is scalable to varying widths.

While various preferred embodiments have been described, those skilled in the art will recognize modifications or variations which might be made without departing from the inventive concept. The examples illustrate the disclosure and are not intended to limit it. Therefore, the description and claims should be interpreted liberally with only such limitation as is necessary in view of the pertinent prior art.

What is claimed is:

1. A method of inspecting material laid by a material placement machine comprising:
    moving the placement machine to cause a frame attached above and behind a compaction device of the machine to overhang a section of the laid material;
    directing light from one or more light sources mounted in the frame onto the laid section in a direction essentially normal to the laid section to illuminate the laid section;
    projecting laser energy from one or more laser sources mounted to the frame onto the section at an angle predetermined to reveal inconsistencies in the section; and
    using one or more cameras mounted above one or more transparent sections of a mirror mounted inside the frame to image the illuminated section through the one or more transparent sections.

2. The method of claim 1, wherein directing light comprises:
    projecting the light toward a reflective surface mounted inside the frame; and
    using the reflective surface to direct the projected light onto the material.

3. The method of claim 2, wherein the light is projected essentially parallel to an axis along which the placement machine moves.

4. The method of claim 1, wherein projecting laser energy comprises projecting one or more laser lines onto the section.

5. The method of claim 1, wherein projecting laser energy comprises extending at least a portion of each of the one or more laser sources below a lower edge of the frame.

6. The method of claim 1, further comprising selecting a number of the light sources and a number of the laser sources for performing the directing and projecting steps, the selecting performed based on a width of the section.

7. A system for inspecting material laid by a material placement machine, the system comprising:
    a frame mounted to the placement machine and configured to extend over a section of material compacted by a compaction device of the placement machine;
    a mirror mounted inside the frame at an angle configured to cause the mirror to reflect horizontally directed light onto the compacted section in a direction substantially normal to the compacted section;
    one or more light sources mounted in the frame and configured to project light horizontally onto the mirror
    one or more laser sources mounted to the frame and configured to project laser energy onto the compacted section at an angle predetermined to reveal inconsistencies in the section; and
    one or more cameras mounted to the frame and configured to image the compacted section through the frame while the section is illuminated by the light and laser sources.

8. The system of claim 7, wherein the one or more cameras are configured to image the laid material based on movement of the placement machine.

9. The system of claim 8, wherein the mirror comprises one or more transparent portions through which the one or more cameras are configured to record the section.

10. The system of claim 8, wherein the one or more laser sources project one or more laser stripes onto the section.

11. The system of claim 7, wherein the one or more light sources are configured to project light essentially parallel to a surface over which the placement machine travels.

12. The system of claim 7, comprising a number of light sources and a number of laser sources configured based on a width of the section.

13. The system of claim 7, wherein the one or more light and one or more cameras are at least partially shielded by the frame.

14. A system for inspecting material laid by a material placement machine, the system comprising:
   a mirror suspended over a section of the material that has been laid, the mirror having one or more transparent portions and mounted in a frame attached above and behind a compaction device of the machine;
   one or more light sources mounted in the frame and configured to project light onto one or more reflective portions of the mirror, the mirror further configured to reflect the projected light onto the material section in a direction essentially normal to the section;
   one or more laser sources mounted to the frame and configured to project laser energy onto the section at an angle predetermined to reveal inconsistencies in the section; and
   one or more cameras mounted in the frame above the mirror and configured to record the section through the one or more transparent portions of the mirror.

15. The system of claim 14, wherein the one or more light sources are configured to project light along an axis of placement of the material.

16. The system of claim 14, wherein the one or more laser sources are configured to project light along an axis of placement of the material.

17. The system of claim 14, wherein the one or more laser sources are configured to project one or more laser lines onto the section.

18. The system of claim 14, wherein the one or more cameras are at least partly shielded by the frame.

19. The system of claim 14, scalable in accordance with a width of the section.

* * * * *